United States Patent
Wenxu et al.

(10) Patent No.: US 10,541,178 B2
(45) Date of Patent: Jan. 21, 2020

(54) METHOD AND DEVICE FOR EVALUATING QUALITY OF THIN FILM LAYER

(71) Applicant: SAMSUNG ELECTRONICS CO., LTD., Suwon-si (KR)

(72) Inventors: Xianyu Wenxu, Suwon-si (KR); Yongyoung Park, Hwaseong-si (KR); Kideok Bae, Seoul (KR); Wooyoung Yang, Hwaseong-si (KR); Changseung Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 149 days.

(21) Appl. No.: 15/635,990

(22) Filed: Jun. 28, 2017

(65) Prior Publication Data

US 2018/0190909 A1    Jul. 5, 2018

(30) Foreign Application Priority Data

Jan. 5, 2017  (KR) .................. 10-2017-0002062

(51) Int. Cl.
| | |
|---|---|
| *H01L 21/66* | (2006.01) |
| *H01L 51/00* | (2006.01) |
| *H01L 51/52* | (2006.01) |
| *H01L 21/67* | (2006.01) |

(52) U.S. Cl.
CPC .............. *H01L 22/12* (2013.01); *H01L 22/20* (2013.01); *H01L 22/26* (2013.01); *H01L 51/0031* (2013.01); *H01L 51/5253* (2013.01); *H01L 21/67288* (2013.01)

(58) Field of Classification Search
CPC ..... H01L 22/12; H01L 22/20; H01L 51/0031; H01L 51/5253; H01L 51/5256; H01L 22/24; H01L 22/26
See application file for complete search history.

(56) References Cited

U.S. PATENT DOCUMENTS

| | | | |
|---|---|---|---|
| 8,711,349 B2 | 4/2014 | Gao et al. | |
| 2002/0106819 A1* | 8/2002 | Nozawa | .................. H01L 22/20 438/14 |
| 2004/0150827 A1 | 8/2004 | Potyrailo et al. | |
| 2006/0078677 A1* | 4/2006 | Won | .......................... C23C 8/36 427/248.1 |
| 2010/0294024 A1 | 11/2010 | Kumar et al. | |
| 2011/0018563 A1 | 1/2011 | Reese et al. | |
| 2015/0371906 A1 | 12/2015 | Kishi et al. | |
| 2017/0088951 A1* | 3/2017 | Dickey | ................. C23C 16/403 |

FOREIGN PATENT DOCUMENTS

| | | | |
|---|---|---|---|
| JP | 06120205 A | * | 4/1994 |
| KR | 10-2006-0117674 A | | 11/2006 |
| KR | 10-2009-0044563 A | | 5/2009 |

* cited by examiner

*Primary Examiner* — Robert G Bachner
*Assistant Examiner* — Molly K Reida
(74) *Attorney, Agent, or Firm* — Sughrue Mion, PLLC

(57) ABSTRACT

A method of evaluating the quality of a thin film layer may include: forming the thin film layer on a substrate; applying a stress to the thin film layer; and evaluating the quality of the thin film layer. A device for evaluating the quality of the thin film layer may include a stress chamber for applying a stress to the thin film layer and a refractive index measuring unit for evaluating the quality of the thin film layer based on a rate of change of a refractive index.

11 Claims, 33 Drawing Sheets

METHOD AND DEVICE FOR EVALUATING QUALITY OF THIN FILM LAYER

CROSS-REFERENCE TO RELATED APPLICATION

This application claims priority from Korean Patent Application No. 10-2017-0002062, filed on Jan. 5, 2017 in the Korean Intellectual Property Office, the entire disclosure of which is incorporated herein by reference.

BACKGROUND

1. Field

Methods and apparatuses consistent with the present disclosure relate to evaluating the quality of a thin film layer.

2. Description of the Related Art

The functionality of various electronic devices may be adversely affected as a result of an external impact or as a result of moisture infiltration. Accordingly, research is underway with respect to the development of an encapsulating layer for protecting electronic devices. Recently, various electronic devices using organic light emitting diodes (OLEDs) including organic materials have been developed.

Since the organic materials used in such OLEDs are easily oxidization by moisture, encapsulation technology is needed to protect the OLED from moisture infiltration. In the case of a rigid OLED, glass encapsulation technology is used to protect devices, which involves covering the devices with glass. In the case of a flexible OLED, thin film encapsulation technology, protecting devices by using a thin film coating, may be used.

In order to evaluate the quality of a thin film layer, water vapor transmission rate (WVTR) methods using calcium (Ca), or oxygen transmission rate (OTR) methods have been conventionally used. However, since the WVTR methods and the OTR methods evaluate the quality of a thin film layer on a plastic substrate, conventional semiconductor processes may not be easily used. In addition, since the WVTR methods or the OTR methods need long evaluation times, ranging from hundreds to thousands of hours, it may be difficult to obtain a speedy evaluation of quality. In addition, since the sample size for such an evaluation is small, it may be difficult to obtain an accurate evaluation of the quality of a larger-sized thin film layer.

SUMMARY

Exemplary embodiments provide methods and apparatuses for evaluating the quality of a thin film layer.

Additional aspects will be set forth in part in the description which follows and, in part, will be apparent from the description, or may be learned by practice of the presented exemplary embodiments.

According to an aspect of an exemplary embodiment, there is provided a method of evaluating the quality of a thin film layer, the method may include: forming the thin film layer on a substrate; applying a stress to the thin film layer; and evaluating the quality of the thin film layer.

The stress may be at least one of a pressure stress, a temperature stress, a humidity stress, an optical stress, a tension stress, a compression stress, and an oxygen stress.

The thin film layer may be formed via a thin film encapsulation process.

The evaluating of the quality of the thin film layer may include evaluating the quality based on a rate of change of a refractive index.

The evaluating of the quality of the thin film layer may include determining that the thin film layer is stable when the rate of change of the refractive index is less than about 5%.

The method may further include: preparing a pinhole detecting layer between the substrate and the thin film layer; measuring the number of impurities n1 on a surface of the thin film layer before applying the stress; selectively etching the pinhole detecting layer after applying the stress; and measuring the number of impurities n2 on the surface of the thin film layer after the etching.

The evaluating of the quality of the thin film layer may include measuring the number of pinholes in the thin film layer by calculating n2−n1.

The etching may include selectively etching the pinhole detecting layer by using an etching solution that reacts with the pinhole detecting layer but does not react with the thin film layer.

The pinhole detecting layer may include an indium gallium zinc oxide (IGZO) material.

The method may further include preparing or providing a device between the substrate and the thin film layer.

The device may be any one of a transistor, an organic photodiode, and a solar cell.

The evaluating the quality of the thin film layer may include evaluating the quality based on a rate of change of electrical characteristics of the device.

When the device is the organic photodiode, the evaluating the quality of the thin film layer may include evaluating the quality based on external quantum efficiency change rates or dark current change rates of the device before and after applying the stress.

The evaluating the quality of the thin film layer may include determining that the quality of the thin film layer is stabilized when the external quantum efficiency change rate is less than about 5% or the dark current change rate is less than about 5%.

The forming of the thin film layer may include forming the thin film layer using a fabrication condition of the thin film layer, and the evaluating of the quality of the thin film layer may include evaluating a degree of quality deterioration in the thin film layer and comparing the degree of quality deterioration with a predetermined critical value.

The evaluating the quality of the thin film layer may determine that the fabrication condition of the thin film layer is adequate when the degree of damage is less than the predetermined critical value, and a result of the evaluating the quality of the thin film layer may be used to change the fabrication condition of the thin film layer when the degree of damage is equal to or greater than the predetermined critical value.

The stress may be applied under pressure cooker test (PCT) conditions.

The substrate may be a wafer substrate including a plurality of chips, and the thin film layer may be formed on the plurality of chips.

According to an aspect of another embodiment, there is provided a device for evaluating the quality of a thin film layer, the device may include: a refractive index measuring unit including a light source configured to emit light that is incident on a thin film layer and a sensor configured to receive refracted light from the thin film layer; and a stress chamber configured to prepare the thin film layer therein and including a first opening through which light from the light source passes and a second opening through which the refracted light from the thin film layer passes.

The stress chamber may further include a first glass which seals the first opening and allows the light from the light source to pass through the first glass, and a second glass which seals the second opening and allows the light refracted from the thin film layer to pass through the second glass.

BRIEF DESCRIPTION OF THE DRAWINGS

These and/or other aspects will become apparent and more readily appreciated from the following description of exemplary embodiments, taken in conjunction with the accompanying drawings in which.

DETAILED DESCRIPTION

Figure 1:
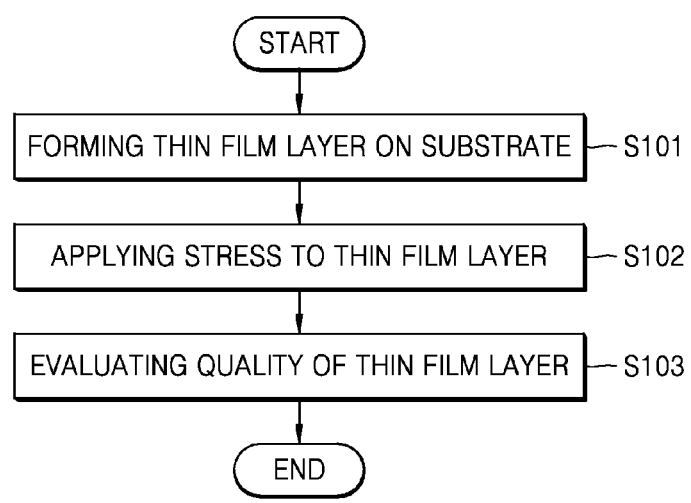
FIG. 1 is a flowchart of a method of evaluating the quality of a thin film layer according to an exemplary embodiment.

Reference will now be made in detail to exemplary embodiments, examples of which are illustrated in the accompanying drawings, wherein like reference numerals refer to like elements throughout. In this regard, the present embodiments may have different forms and should not be construed as being limited to the descriptions set forth herein. Accordingly, the exemplary embodiments are merely described below, by referring to the figures, to explain certain aspects thereof. Expressions such as "at least one of," when preceding a list of elements, modify the entire list of elements and do not modify the individual elements of the list.

Methods and apparatuses for evaluating the quality of a thin film layer according to exemplary embodiments will now be described more fully with reference to the accompanying drawings. In the drawings, the thicknesses and widths of layers and regions are exaggerated for clarity.

While this disclosure has been particularly shown and described with reference to exemplary embodiments, it will be understood by those of ordinary skill in the art that various changes in form and details may be made therein without departing from the spirit and scope of the disclosure as defined by the appended claims. The exemplary embodiments should be considered to be descriptive only, and do not serve to limit the present disclosure. Therefore, the scope of the disclosure is defined not only by the detailed description of the disclosure but also by the appended claims, and all differences between the two should be construed as being included in the disclosure.

While such terms as "first," "second," etc., may be used to describe various components, the above terms are used only to distinguish one component from another.

As used herein, the singular forms "a," "an" and "the" are intended to include the plural forms as well, unless the context clearly indicates otherwise. When an item is described as, e.g., including or being composed of something, it should be understood that the item may further include other elements unless the context clearly indicates otherwise.

FIG. 1 is a flowchart of a method of evaluating the quality of a thin film layer, according to an exemplary embodiment. Referring to FIG. 1, the method of evaluating the quality of a thin film layer may include forming the thin film layer on a substrate (S101), applying stress to the thin film layer (S102), and evaluating the quality of the thin film layer (S103).

The forming of the thin film layer on the substrate (S101) may include forming the thin film layer on a silicon substrate or a wafer substrate. The thin film layer may be formed by using a conventional semiconductor process or a display process. The thin film layer may be formed on a portion of the silicon substrate or the wafer substrate, or may be formed on an entirety of the substrate. As an example, the thin film layer may be a passivation layer for protecting the substrate from being damaged. The thin film layer may also serve to prevent the substrate from being damaged by moisture, oxygen, or an outside impact. As an example, the forming of the thin film layer may be executed by the thin film encapsulation process. For example, the thin film layer may be formed by depositing an acrylic monomer on the substrate via an evaporation process, by curing the acrylic monomer via infrared beams, and by depositing aluminum oxide ($AL_2O_3$) on the acrylic monomer via a sputtering process. A detailed formulation condition of the thin film layer may use a predetermined formulation condition of the thin film layer. For example, the formulation condition of the thin film layer may be determined by values of variables in the forming process of the thin film layer. The fabrication condition may comprise any type of condition that can affect a fabrication process. For example, variables of the fabrication condition may comprise a fabrication temperature, pressure, humidity, oxygen concentration, gas concentration (i.e. $N_2O$) gas flow speed, and the like. It should be understood that the examples of the variables described herein should be considered to be descriptive only and do not limit the variables. Those skilled in the art can easily understand what types of variables can affect a fabrication process, and those variables can be understood as being variables of the fabrication condition.

When the thin film layer is formed, various defects may occur on a surface of the thin film layer. The defects may include, e.g., particles, cracks, pinholes, etc. When stress is applied to the thin film layer, more defects than the number of defects which may normally occur at the time of forming the thin film layer may occur. For example, when stress is applied, pinholes may occur in the thin film layer. For example, a refractive index on the surface of the thin film layer may be changed, and/or a thickness of the thin film layer may be changed. When the thin film layer is formed in accordance with adequate conditions, the thin film layer may not have the defects described above. Adequate fabrication conditions of the thin film layer (i.e., conditions under which the thin film layer may be formed) may be derived by changing the fabrication conditions of the thin film layer until the number of defects is less than a critical value. Derivation of the adequate fabrication conditions of the thin film layer will be described later with reference to FIG. 32.

A device may be formed between the thin film layer and the substrate. For example, the device may be any one of a transistor, an organic photodiode, and a solar cell. In certain aspects, the device may be formed on the substrate and the thin film layer may be formed on the device. The quality of the thin film layer may be evaluated by forming the device directly on the substrate under conditions similar to an actual usage state of the device.

The applying of the stress to the thin film layer (S102) may include applying the stress when forming the thin film layer (S101). For example, the stress may be any one or more of a pressure stress, a temperature stress, and a humidity stress. The stress may also be any one or more of an optical stress, a tension stress, a compression stress, and an oxygen stress. The stress may be any kind of stress that may cause damage to the thin film layer, and the current exemplary embodiment is not limited to the examples above. As an example, the stress may be applied to the thin film layer while under pressure cooker test (PCT) conditions. The PCT conditions may be, for example, a temperature of about 121±about 2° C., humidity of from about 98 to about 100%, and pressure of about 2±about 0.2 atm.

The evaluating of the quality of the thin film layer (S103) may include evaluating the quality of the thin film layer by evaluating defects in the thin film layer after the stress has been applied to the thin film layer. For example, the quality of the thin film layer may be evaluated by comparing a degree of quality deterioration of the thin film layer with a predetermined critical value. For example, the degree of the quality deterioration may include a rate of change of a refractive index (hereinafter, a refractive index change rate), a thickness change rate, and the number of pinholes. For example, when determining the refractive index change rate, the quality of the thin film layer may be evaluated by calculating a ratio of refractive indices on the surface of the thin film layer before and after the stress is applied. For example, when determining the thickness change rate, the quality of the thin film layer may be evaluated by calculating a ratio of thicknesses of the surface of the thin film layer before and after the stress is applied. For example, when determining the number of pinholes, the quality of the thin film layer may be evaluated by counting the number of pinholes on the surface of the thin film layer.

When the device is formed on the substrate and the thin film layer is formed on the device, the quality of the thin film layer may be evaluated by evaluating electric characteristics of the device. For example, the quality of the thin film layer may be evaluated by comparing external quantum efficiencies of the device before and after the stress is applied. For example, the quality of the thin film layer may also be evaluated by comparing dark currents of the device before and after the stress is applied.

Figure 2:
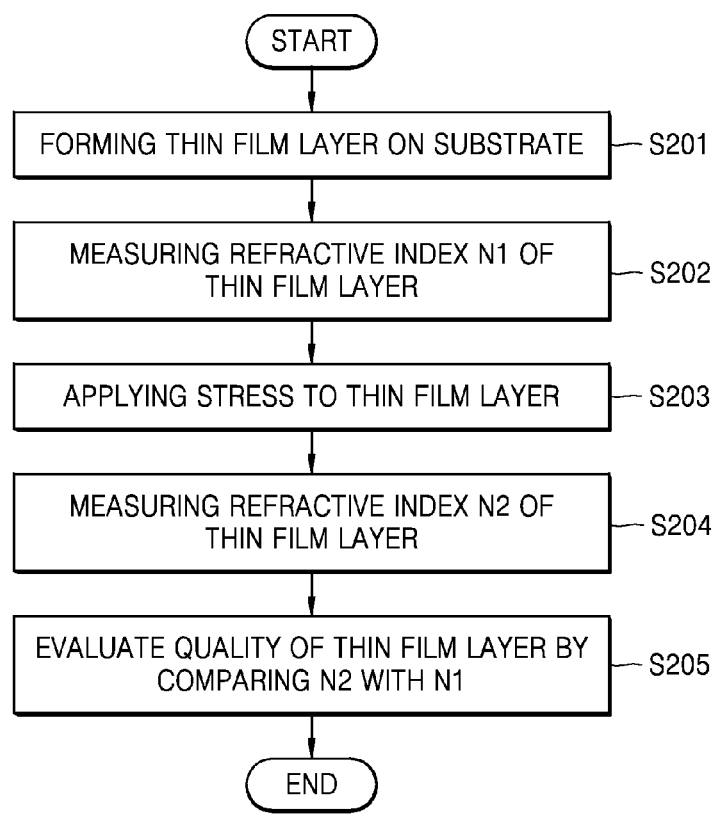
FIG. 2 is a flowchart of a method of evaluating the quality of a thin film layer according to another exemplary embodiment.

FIG. 2 is a flowchart of a method of evaluating the quality of a thin film layer according to another exemplary embodiment. FIGS. 3 through 8 are cross-sectional views illustrating the method of evaluating the quality of a thin film layer according to FIG. 2

Referring to FIG. 2, a refractive index n1 of the surface of the thin film layer may be measured (S202) after the forming the thin film layer (S201). Next, after stress is applied to the thin film layer (S203), a refractive index n2 of the surface of the thin film layer may be measured (S204). The quality of the thin film layer may be evaluated by comparing n2 with n1 (S205).

Figure 3:
FIGS. 3 through 8 are cross-sectional views illustrating the method of evaluating the quality of a thin film layer according to FIG. 2.

Referring to FIG. 3, the substrate SUB may be prepared.

Figure 4:
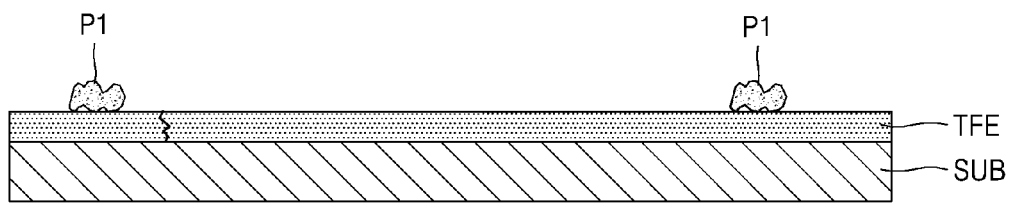

Referring to FIG. 4, a thin film layer TFE may be formed on the substrate SUB. The thin film layer TFE may be formed by encapsulating the substrate SUB. The thin film layer TFE may be formed in accordance with the predetermined fabrication condition of the thin film layer TFE. When the fabrication condition of the thin film layer TFE is not adequate, there may be defects in the thin film layer TFE. For example, there may be particles P1 or pinholes P2 (see FIG. 7) on the thin film layer TFE.

Figure 5:
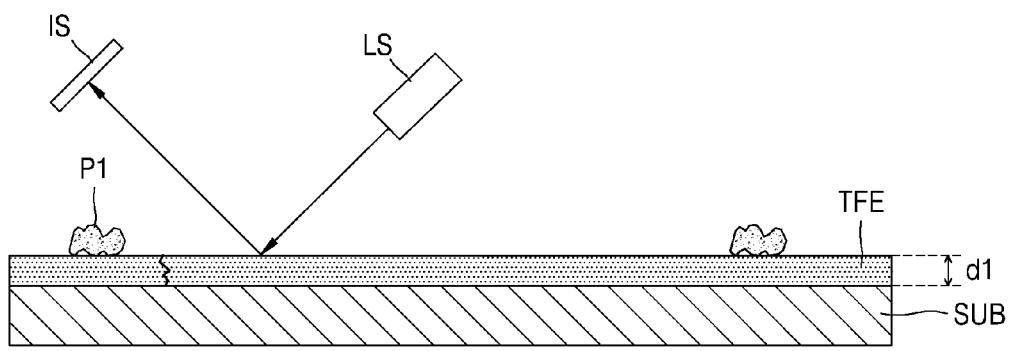

Referring to FIG. 5, the refractive index n1 of the thin film layer TFE may be measured. The refractive index n1 may be measured by radiating light onto the surface of the thin film layer TFE from a light source LS and receiving a reflected beam at an image sensor IS. The use of light source LS and image sensor IS is only an example of how the refractive index may be measured, and the present exemplary embodiment is not limited thereto. In addition, referring to FIG. 5, a thickness dl of the thin film layer TFE may be measured. According to an exemplary embodiment, the method of evaluating the quality of the thin film layer TFE may include simultaneously measuring both the refractive index n1 and the thickness dl. However, the present exemplary embodiment is not limited thereto. The method of evaluating the quality of the thin film layer TFE may include measuring only the refractive index n1 or only the thickness dl.

Figure 6:
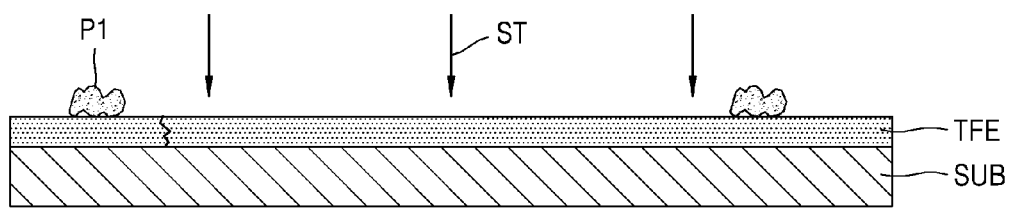

Referring to FIG. 6, a stress ST may be applied (shown by arrows) to the thin film layer TFE. The stress ST may be any one or more of a pressure stress, temperature stress, humidity stress, optical stress, tension stress, compression stress, and oxygen stress. For example, the stress ST may be applied to the thin film layer TFE such that the PCT conditions are satisfied. For example, when the stress ST satisfying the PCT conditions is applied to the thin film layer TFE, the quality of the thin film layer TFE may be evaluated within a few dozen hours.

Figure 7:
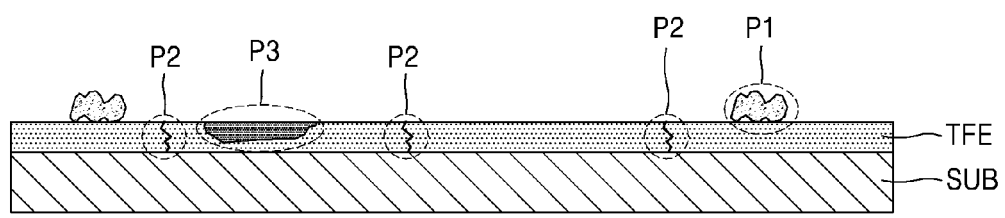

Referring to FIG. 7, after the stress ST is applied to the thin film layer TFE, defects in the thin film layer may be present. The defects may be in the form of the particles P1 or pinholes P2 which occur when forming the thin film layer, and a refractive index change region P3 including a higher number of pinholes P2 may be present in the thin film layer TFE. A pinhole P2 may be a small hole having a size on the order of nanometers formed in the thin film layer TFE. Since moisture or oxygen may pass through a pinhole P2, the substrate SUB may be damaged if pinholes are present. The refractive index change region P3 may be a region in which the refractive index of the thin film layer TFE is changed as a result of the stress ST applied to the thin film layer TFE. According to the illustration in FIG. 7, the refractive index change region P3 may be formed in a portion of the thin film layer TFE. However, the present exemplary embodiment is not limited thereto. The refractive index change region P3 may be formed in the entire portion of the thin film layer TFE. Both the refractive index and the thickness may be changed in the refractive index change region P3. For example, the thickness of the substrate may be changed from dsub1 to dsub2 (not shown) in the refractive index change region P3. The reason for this is that the materials in the original thin film layer TFE may be changed as a result of the applied stress ST, and thus the materials of the refractive index change region P3 may be altered from the materials of the original thin film layer TFE, leading to changes in the refractive index and density of the refractive index change region P3.

Figure 8:
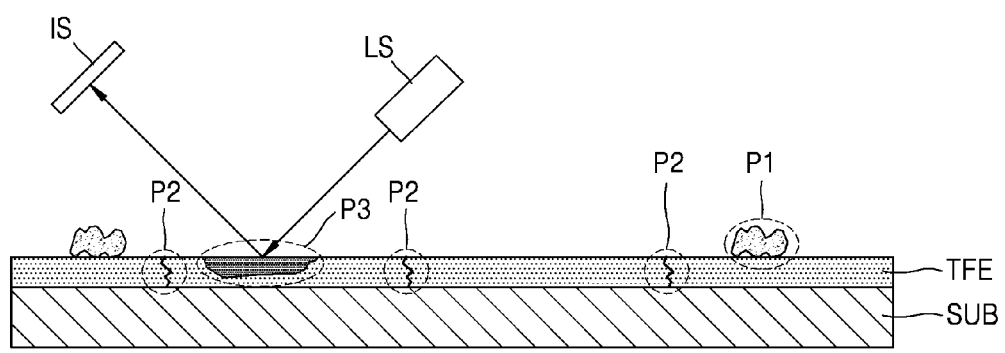

Referring to FIG. 8, the refractive index n2 may be measured by measuring the refractive index of the refractive index change region P3. The refractive index change rate may be measured by comparing refractive indices n2 with n1, and the quality of the thin film layer TFE may be evaluated based on the measured refractive index change rate. When the refractive index change rate is equal to or greater than a critical value, the quality of the thin film layer may be evaluated as being "unstable". When the refractive index change rate is less than the critical value, the quality of the thin film layer may be evaluated as being "stable". The critical value, which is a value for evaluating the quality of the thin film layer TFE as "stable" or "unstable", may be established by experiments and theories. For example, when the refractive index change rate is equal to or greater than 5%, the quality of the thin film layer may be evaluated as "unstable", and when the refractive index change rate is less than 5%, the quality of the thin film layer may be evaluated as "stable". The value provided herein is only an example and is not limited thereto.

As described above, the thickness as well as the refractive index of the refractive index change region P3 may be changed. For example, the thickness of the refractive index change region P3 may be changed from dric1 to dric2 due to the applied stress ST. The quality of the thin film layer may be evaluated by measuring the thickness change rate of the refractive index change region P3. When the thickness change rate is equal to or greater than a critical value, the quality of the thin film layer may be evaluated as "unstable". When the thickness change rate is less than the critical value, the quality of the thin film layer may be evaluated as "stable". For example, when the thickness change rate is equal to or greater than 5%, the quality of the thin film layer may be evaluated as "unstable", and when the thickness change rate is less than 5%, the quality of the thin film layer may be evaluated as "stable". The value provided herein is only an example and is not limited thereto.

Figure 9:
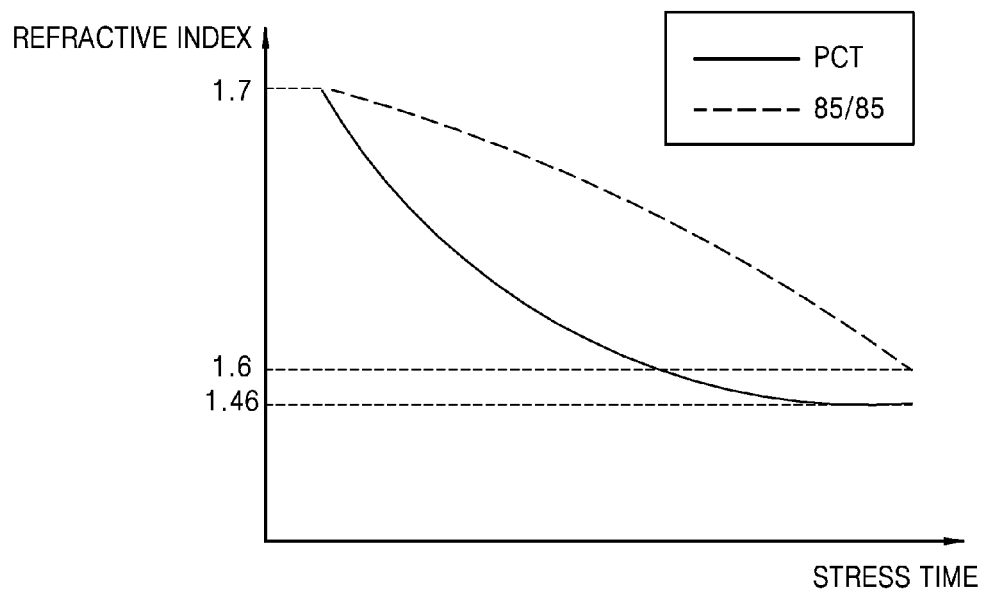
FIG. 9 is a graph comparing a method of evaluating the quality of a thin film layer according to an exemplary embodiment with a conventional method of evaluating the quality of a thin film layer.

FIG. 9 is a graph comparing a method of evaluating the quality of a thin film layer according to an exemplary embodiment with a conventional method of evaluating the quality of a thin film layer.

Referring to FIG. 9, the vertical axis denotes the refractive index of the thin film layer and the horizontal axis denotes the time over which stress was applied. According to the result of an experiment measuring the refractive index by using light having a wavelength of about 550 nm, the refractive index of a thin film layer was about 1.7 at the beginning of the application of a stress, and changed to a level of about 1.6 after a PCT stress was applied for less than about 10 hours. On the other hand, the refractive index of the thin film layer was changed to a level of about 1.6 when a temperature stress of about 85° C. and a humidity stress of about 85% (denoted "85/85" in FIG. 9) were applied for about 700 hours or longer. Thus, when testing the refractive index change based on stress time, application of the PCT stress conditions may decrease a testing time period by more than 98 percent, when compared with the use of an 85/85 temperature/humidity stress. In addition, when the initial refractive index is defined as $n_s$ and a final refractive index is defined as $n_f$, the refractive index change rate may be defined by the formula, $(n_s-n_f)/n_s*100$. Thus, when a thin film layer sample according to an exemplary embodiment satisfies the formula, $(n_s-n_f)/n_s*100 \geq 5\%$, the quality of the thin film layer sample may be evaluated as "unstable". In this case, the fabrication condition of the thin film layer may not be an adequate fabrication condition and the fabrication condition may be changed. On the other hand, when the thin film layer sample satisfies the formula, $(n_s-n_f)/n_s*100 < 5\%$, the quality of the thin film layer may be evaluated as "stable".

Figure 10:
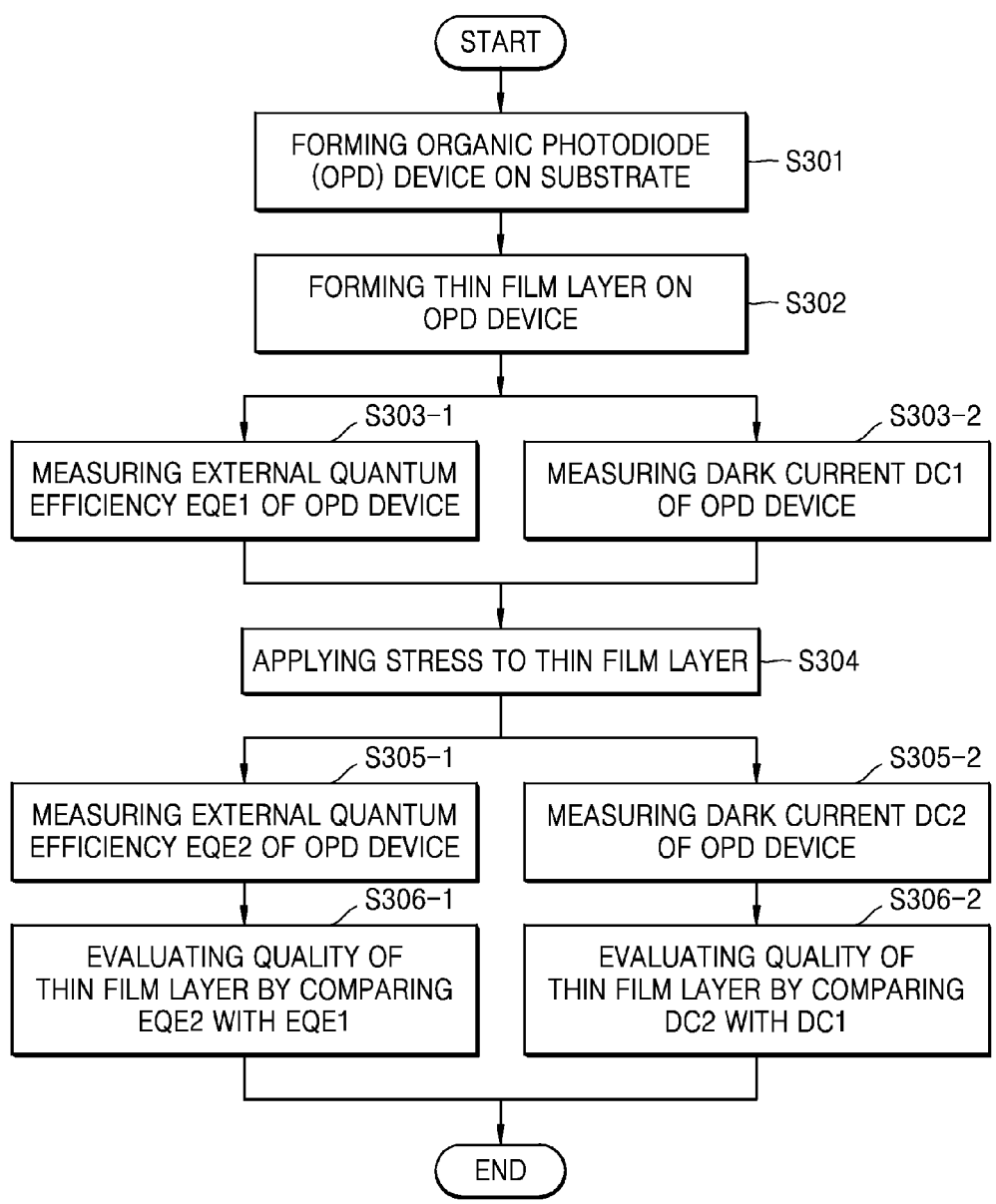
FIG. 10 is a flowchart of a method of evaluating the quality of a thin film layer according to another exemplary embodiment.

FIG. 10 is a flowchart of a method of evaluating the quality of a thin film layer according to another exemplary embodiment. FIGS. 11 through 18 are drawings illustrating the method of evaluating the quality of a thin film layer according to FIG. 10.

Referring to FIG. 10, an organic photodiode (OPD) device may be formed on a substrate (S301), and a thin film layer may be formed on the OPD device (S302). An external quantum efficiency EQE1 of the OPD device may be measured (S303-1) or a dark current DC1 of the OPD device may be measured (S303-2). Next, stress may be applied to the thin film layer (S304), and an external quantum efficiency EQE2 of the OPD device may be measured (S305-1) or the dark current DC2 of the OPD device may be measured (S305-2). The quality of the thin film layer may be evaluated by comparing the external quantum efficiencies EQE2 with EQE1 (S306-1) or by comparing the dark currents DC2 with DC1 (S306-2).

Figure 11:
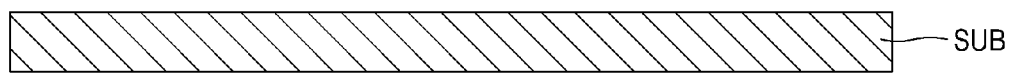
FIGS. 11 through 18 are drawings illustrating the method of evaluating the quality of a thin film layer according to the exemplary embodiment of FIG. 10.

Referring to FIG. 11, the substrate SUB may be prepared.

Figure 12:
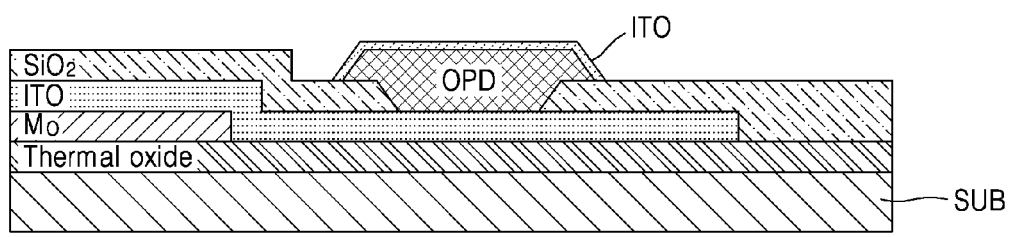

Referring to FIG. 12, the OPD device may be prepared on the substrate SUB. The OPD device may include a thermal oxide, a molybdenum (Mo) layer, an indium-tin-oxide (ITO) electrode, a silicon dioxide ($SiO_2$), the OPD, etc. Various devices, such as a transistor or a solar cell, may be prepared on the substrate SUB, and are not limited to an OPD device.

Figure 13:
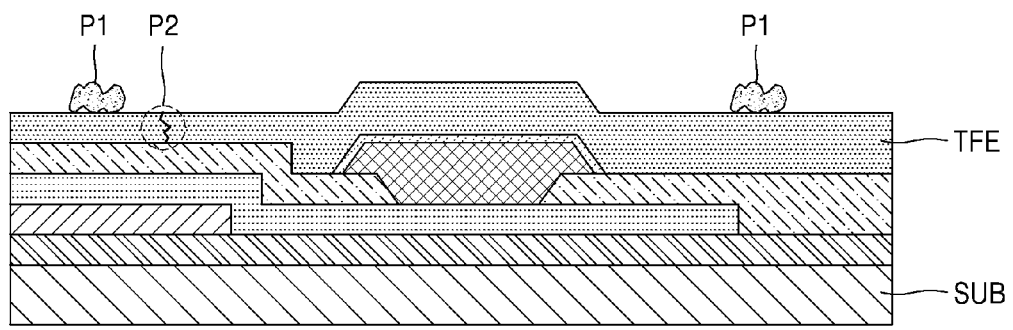

Referring to FIG. 13, the thin film layer TFE may be prepared on the OPD device. The thin film layer TFE may be formed via a thin film encapsulation process. The thin film layer TFE may be formed using a predetermined fabrication condition of the thin film layer. When the thin film fabrication condition is not adequate for forming the thin film, defects may occur in the thin film layer TFE. For example, a particle P1 or a pinhole P2 may occur in the thin film layer TFE.

Figure 14:
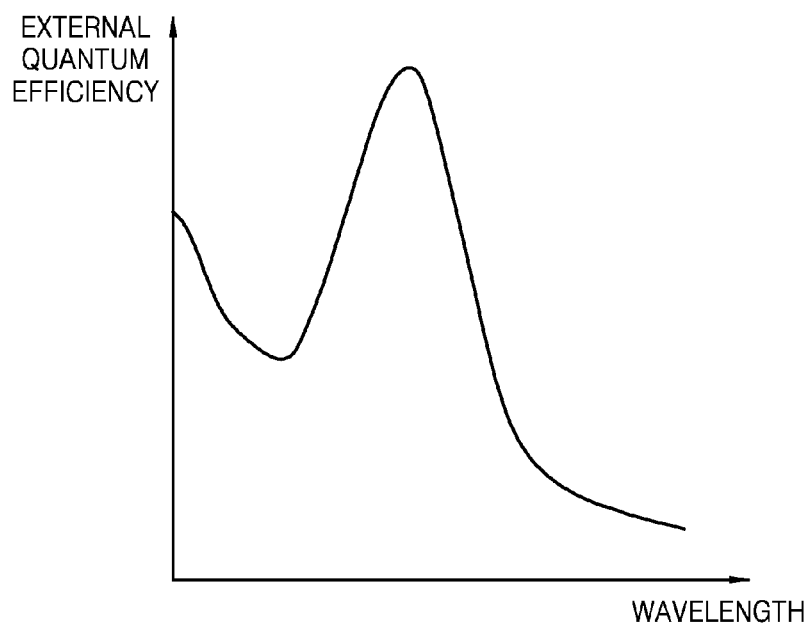

Referring to FIG. 14, an external quantum efficiency, which is one of the electrical characteristics of an OPD device, may be measured. In FIG. 14, the horizontal axis denotes the wavelength and the vertical axis denotes the external quantum efficiency.

Figure 15:

Referring to FIG. 15, the current density, which is one of the electrical characteristics of an OPD device, may be measured. In FIG. 15, the horizontal axis denotes the voltage applied to an electrode and the vertical axis denotes the current density. In FIG. 15, the point having the lowest current density may be a point at which voltage is not applied. When a positive voltage is applied to the OPD device based on the point having the lowest current density, the electrical resistance is high due to a reverse bias voltage and thus, little current may flow. When a forward bias voltage is applied to the OPD device based on the point having the lowest current density, the depletion zone may be reduced and thus current may easily flow. When a reverse bias voltage equal to or less than a critical value is applied, the current density flowing through the OPD device may be defined as the dark current. For example, the dark current DC1 may be measured for identifying electrical characteristics of the OPD device before stress is applied thereto.

Figure 16:
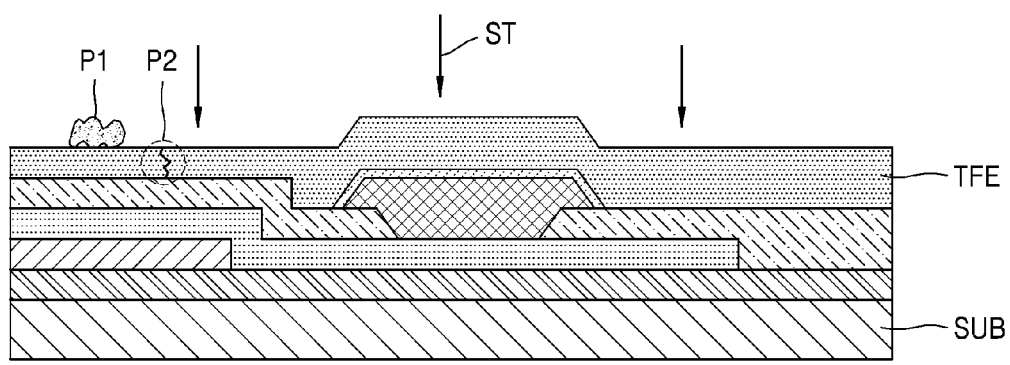

Referring to FIG. 16, the stress ST may be applied to the thin film layer TFE. The stress ST may be any one or more of pressure stress, temperature stress, humidity stress, optical stress, tension stress, compression stress, and oxygen stress. The stress ST may be applied to the thin film layer TFE such that PCT conditions are satisfied. When stress ST satisfying PCT conditions is applied to the thin film layer TFE, the quality of the thin film layer TFE may be evaluated within, for example, a few dozen hours.

Figure 17:
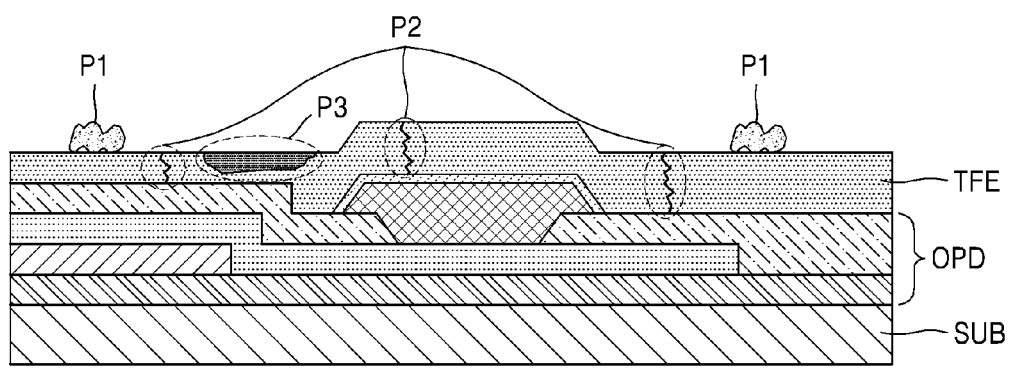

Referring to FIG. 17, after the stress ST is applied, the thin film layer TFE may include more defects. In addition to the particle P1 which was present at the time of forming the thin film layer TFE, increased numbers of pinholes P2, and refractive index change regions P3 may occur in the thin film layer TFE. The pinhole P2 may be a small hole having an opening having a size on the order of nanometers. The pinhole P2 may allow, for example, moisture or oxygen molecules to pass therethrough and thus, the substrate SUB may become damaged. The refractive index change region P3 may be a region in which the refractive index of the thin film layer is changed as a result of exposure to the stress ST. FIG. 17 shows an example in which the refractive index change region P3 occurs in a portion of the thin film layer TFE. However, the refractive index change region P3 is not limited thereto, and may occur in an entire portion of the thin film layer TFE.

As described above with reference to FIGS. 3 through 8, the quality of the thin film layer TFE may be evaluated based on the refractive index change rate of the refractive index change region P3. Detailed descriptions have been provided above and will not be repeated here. Since the quality of the OPD device may also be evaluated based on electrical characteristics, descriptions in this regard are provided below.

Figure 18:
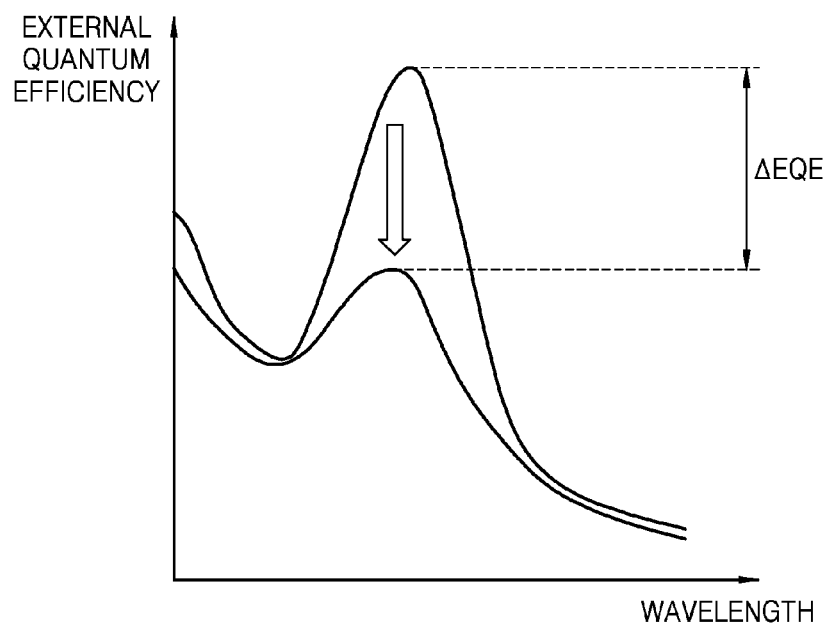

Referring to FIG. 18, an external quantum efficiency change rate ΔEQE may be evaluated by measuring the external quantum efficiency EQE2 of the thin film layer TFE after the stress ST is applied. The external quantum efficiency change rate ΔEQE may be derived by comparing the external quantum efficiencies EQE2 with EQE1. As illustrated, when the stress ST is applied, a peak shape of the external quantum efficiency graph is reduced, and thus, the external quantum efficiency change rate ΔEQE may be evaluated by comparing the peak shapes.

In the method of evaluating the quality of the OPD device, when a value of ΔEQE/EQE1 is equal to or greater than a critical value, the quality of the thin film layer may be evaluated as "unstable", and when the value of ΔEQE/EQE1 is less than the critical value, the quality of the thin film layer may be evaluated as "stable". For example, when the value of ΔEQE/EQE1 is equal to or greater than about 5%, the quality of the thin film layer may be evaluated as "unstable", and when the value of ΔEQE/EQE1 is less than about 5%, the quality of the thin film layer may be evaluated as "stable". As another example, when the value of ΔEQE/EQE1 is equal to or greater than about 3%, the quality of the thin film layer may be evaluated as "unstable", and when the value of ΔEQE/EQE1 is less than about 3%, the quality of the thin film layer may be evaluated as "stable".

In addition, the current density change ΔDC may be measured by measuring the current density DC2 of the thin film layer TFE after the stress ST is applied. The current density change ΔDC may be derived by comparing DC1 with DC2.

In the method of evaluating the quality of the OPD device, when a value of ΔDC/DC1 of the dark current is equal to or greater than the critical value, the quality of the thin film layer may be evaluated as "unstable", and when the value of ΔDC/DC1 of the dark current is less than the critical value, the quality of the thin film layer may be evaluated as "stable". For example, when the value of ΔDC/DC1 of the dark current is equal to or greater than about 5%, the quality of the thin film layer may be evaluated as "unstable", and when the value of ΔDC/DC1 of the dark current is less than about 5%, the quality of the thin film layer may be evaluated as "stable". As another example, when the value of ΔDC/DC1 of the dark current is equal to or greater than about 3%, the quality of the thin film layer may be evaluated as "unstable", and when the value of ΔDC/DC1 of the dark current is less than about 3%, the quality of the thin film layer may be evaluated as "stable".

Figure 19:
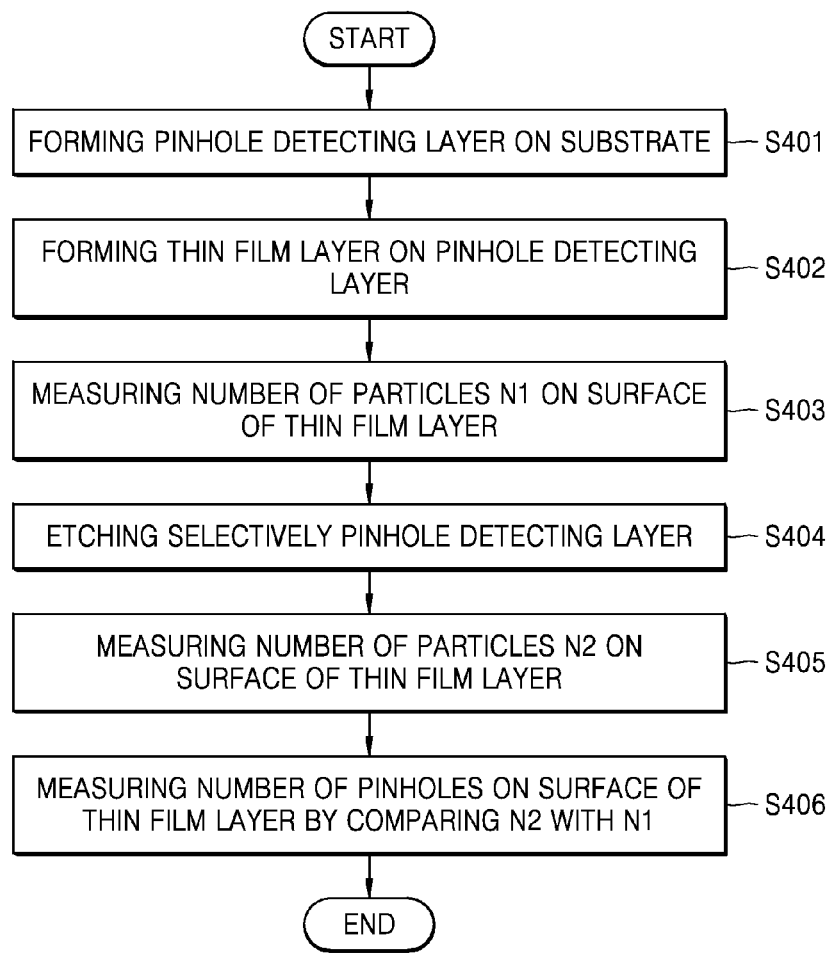
FIG. 19 is a flowchart of a method of evaluating the quality of a thin film layer according to another exemplary embodiment.

FIG. 19 is a flowchart of a method of evaluating the quality of a thin film layer according to another exemplary embodiment. Referring to FIG. 19, the method of evaluating the quality of a thin film layer according to this exemplary embodiment may include forming a pinhole detecting layer on the substrate SUB (S401), forming the thin film layer on the pinhole detecting layer (S402), measuring the number of particles n1 on a surface of the thin film layer (S403), selectively etching the pinhole detecting layer (S404), measuring the number of particles n2 on the surface of the thin film layer (S405), and measuring the number of the pinholes on the thin film layer by comparing n2 with n1 (S406).

The pinhole detecting layer may be a layer which can detect a pinhole in the thin film layer. The pinhole detecting layer may have a different material composition from that of the thin film layer. For example, the pinhole detecting layer may include an IGZO material.

The pinhole detecting layer may be selectively etched. A particular etchant may not react with the thin film layer but may react with the pinhole detecting layer and thus, may selectively etch the pinhole detecting layer. Both the thin film layer and the pinhole detecting layer may be immersed in such an etchant such that only the pinhole detecting layer may be etched. As a result, material from the pinhole detecting layer may be sucked up and hardened on the surface of the thin film layer. The number of pinholes in the thin film layer may be counted by counting the number of pinhole particles formed from the material of the pinhole detecting layer which are hardened on the surface of the thin film layer.

A method of evaluating the quality of a thin film layer according to an exemplary embodiment may include measuring the number of pinholes at the time of forming the thin film layer, without including the application of stress.

Figure 20:
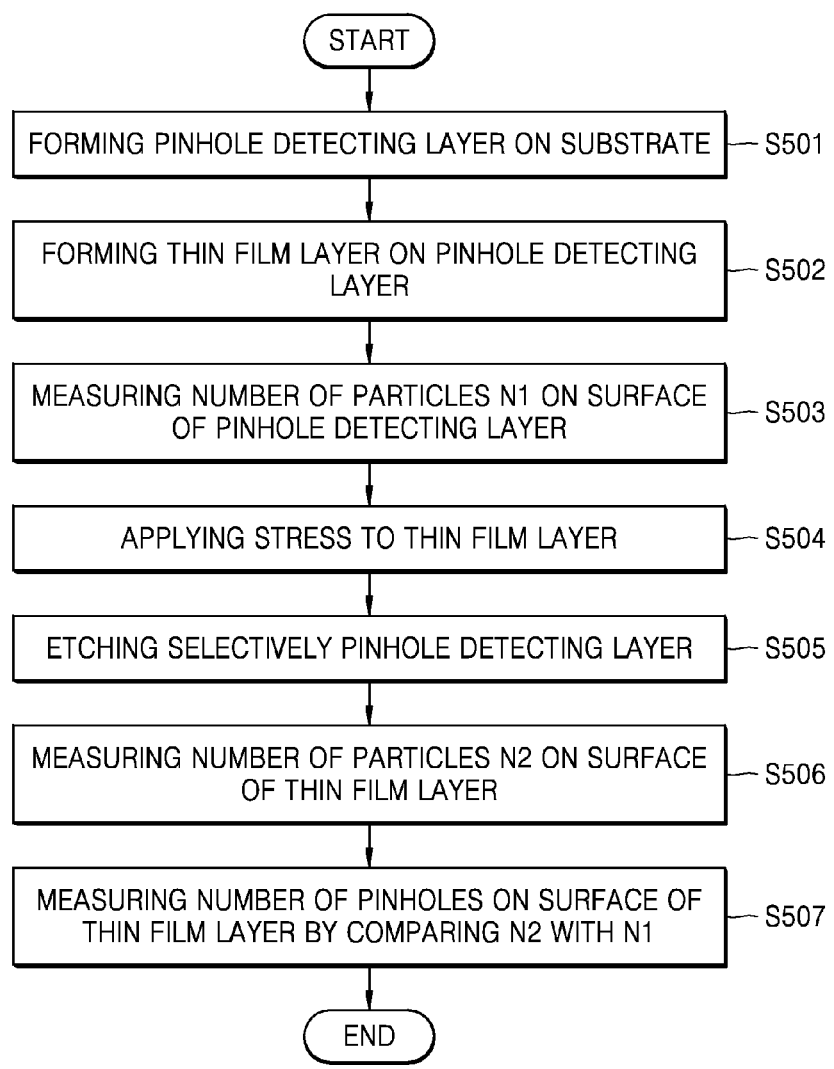
FIG. 20 is a flowchart of a method of evaluating the quality of a thin film layer according to another exemplary embodiment.

FIG. 20 is a flowchart showing a method of evaluating the quality of a thin film layer according to another exemplary embodiment. FIGS. 21 through 29 are cross-sectionals views illustrating the method of evaluating the quality of a thin film layer according to FIG. 20.

Referring to FIG. 20, the method of evaluating the quality of a thin film layer may include forming the pinhole detecting layer PDL on the substrate SUB (S501), forming the thin film layer on the pinhole detecting layer PDL (S502), measuring the number of particles n1 on the surface of the thin film layer (S503), applying stress to the thin film layer (S504), selectively etching the pinhole detecting layer PDL (S505), measuring the number of particles n2 on the surface of the thin film layer (S506), and measuring the number of pinholes on the surface of the thin film layer by comparing n2 with n1 (S507).

The method of evaluating the quality of a thin film layer according to this exemplary embodiment may further include the application of stress (S504), when compared with the method of evaluating the quality of a thin film layer according to FIG. 19. Accordingly, the number of pinholes generated in the thin film layer may be counted at the step of applying the stress (S504).

Figure 21:
FIGS. 21 through 29 are cross-sectional views illustrating the method of evaluating the quality of a thin film layer according to FIG. 20.

Referring to FIG. 21, the substrate SUB may be prepared.

Figure 22:
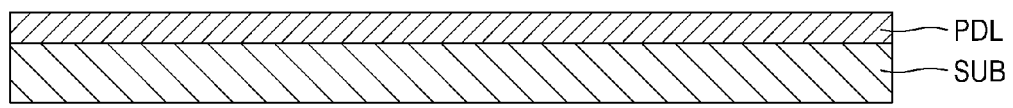

Referring to FIG. 22, the pinhole detecting layer PDL may be prepared on the substrate SUB. The pinhole detecting layer PDL may include a different material than the material of the thin film layer TFE. For example, the pinhole detecting layer PDL may include IGZO.

Figure 23:
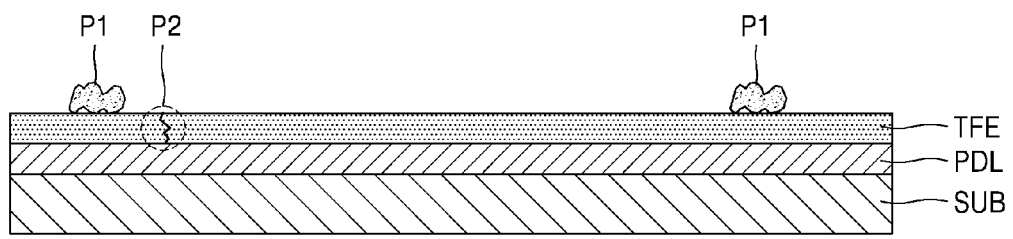

Referring to FIG. 23, the thin film layer TFE may be formed on the pinhole detecting layer PDL. The thin film layer TFE may be formed via a thin film encapsulation process. The thin film layer TFE may include a particle P1 or a pinhole P2. The pinhole P2 may be a hole having a size on the order of a nanometer, which may not be detected by a human eye or by a conventional optical device. The pinhole P2 may allow outside moisture or oxygen infiltrate therethrough and thus, may be a cause of damage to the substrate SUB.

Figure 24:
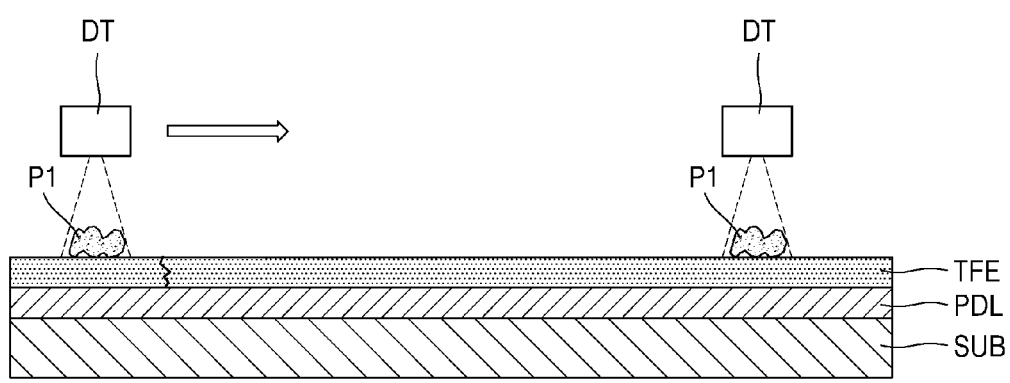

Referring to FIG. 24, the number of particles n1 on the surface of the thin film layer TFE may be measured. For example, the number of particles P1 on the surface of the thin film layer TFE n1 may be measured by using a number detector DT. The type of number detector DT is not particularly limited. For example, the number n1 of the particles P1 may be measured via a conventional optical device.

Figure 25:
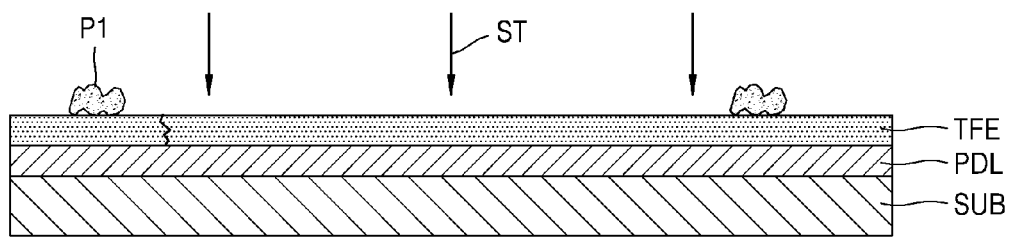

Referring to FIG. 25, stress ST may be applied to the thin film layer TFE. The stress ST may be at least one or more of pressure stress, temperature stress, humidity stress, optical stress, tension stress, compression stress, and oxygen stress. As an example, the stress may be applied to the thin film layer TFE such that PCT conditions are satisfied. When stress satisfying PCT conditions is applied to the thin film layer TFE, the quality of the thin film layer may be evaluated within, for example, dozens of hours.

Figure 26:
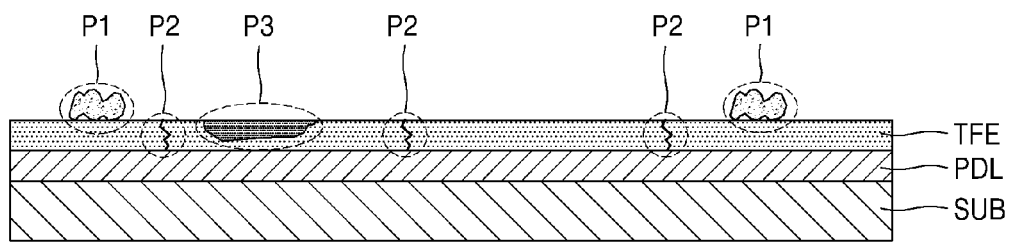

Referring to FIG. 26, after the stress ST is applied, the thin film layer TFE may include more defects. In addition to the particle P1 which have been present at the time of forming the thin film layer TFE, increased numbers of pinhole P2 and refractive index change region P3 may be present in the thin film layer TFE. The pinhole P2 may be a small hole having an opening having a size on the order of a nanometer. The pinhole P2 may allow moisture or oxygen molecules to pass therethrough and thus, may cause damage to the substrate SUB. As illustrated in FIG. 26, the refractive index change region P3 may occur in a portion of the thin film layer TFE. However, the refractive index change region P3 is not limited thereto and may occur in an entire portion of the thin film layer TFE.

As described with reference FIGS. 3 through 8, the quality of the thin film layer TFE may be evaluated based on the refractive index change rate of the refractive index change region P3. In addition, the quality of the thin film layer TFE may also be evaluated via electrical characteristics of the OPD device.

Figure 27:
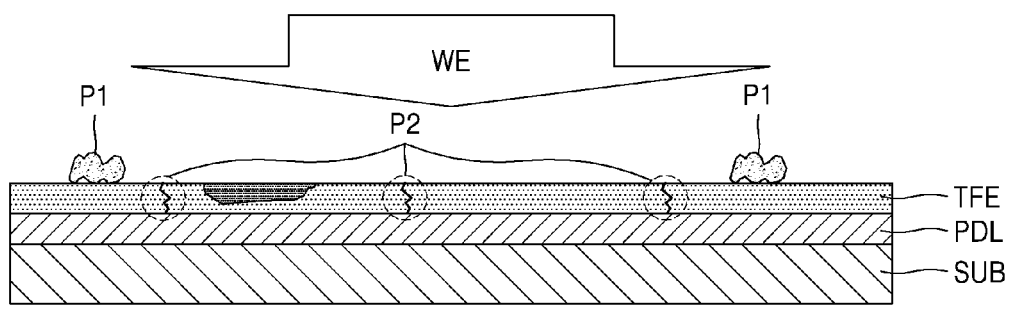

Referring to FIG. 27, the pinhole detecting layer PDL may be selectively etched. For example, the pinhole detecting layer PDL may be etched via wet etching WE. For etching the pinhole detecting layer PDL, the etchant may penetrate the pinhole P2 having a nanometer size and arrive at the pinhole detecting layer PDL. Thus, an etchant having a low viscosity may be selected.

Figure 28:
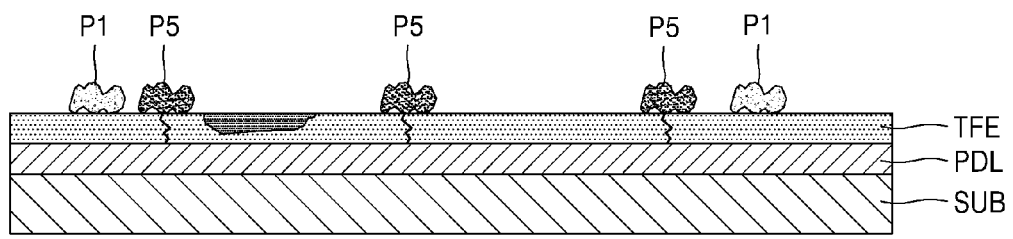

Referring to FIG. 28, a pinhole particle P5 may be formed at each location of pinhole P2 on the thin film layer TFE. The pinhole particle P5 may be a lump of the pinhole detecting layer PDL which has been etched, sucked up along the pinhole P2 and hardened on the thin film layer TFE. Accordingly, not only the particle P1, which was formed at the time of forming the thin film layer TFE, but also particle P5 may exist on the thin film layer TFE.

Figure 29:
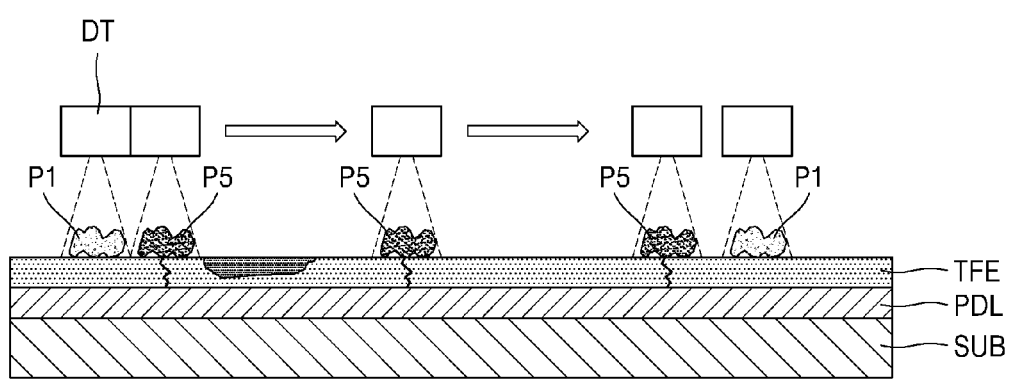

Referring to FIG. 29, the number of particles P1 and P5 on the thin film layer TFE, that is, n2 may be measured. For example, the number of particles P1 and P5 on the thin film layer TFE, n2, may be measured by using number detector DT. Then, the value of n2−n1 may be calculated, and the number of the particles P5, which may be the same as the number of pinholes P2, may be determined. Thus, the number of pinholes P2 on the thin film layer TFE may be measured by calculating the value of n2−n1.

The quality of the thin film layer TFE may be evaluated based on the number of pinholes P2. For example, when the number of pinholes P2, formed under a particular fabrication condition of the thin film layer TFE, is assumed as 100 and the number of the pinholes P2, formed under another fabrication condition of the thin film layer TFE, is assumed as 10, a fabrication condition of the thin film layer TFE having smaller number of the pinholes P2 may be evaluated as being closer to an adequate fabrication condition of the thin film layer. In the method of evaluating the quality of a thin film layer by using the number of pinholes, a critical value may be defined as a number of the pinholes and may be, for example, about 0 or an adequate number determined by experimentation.

Figure 30:
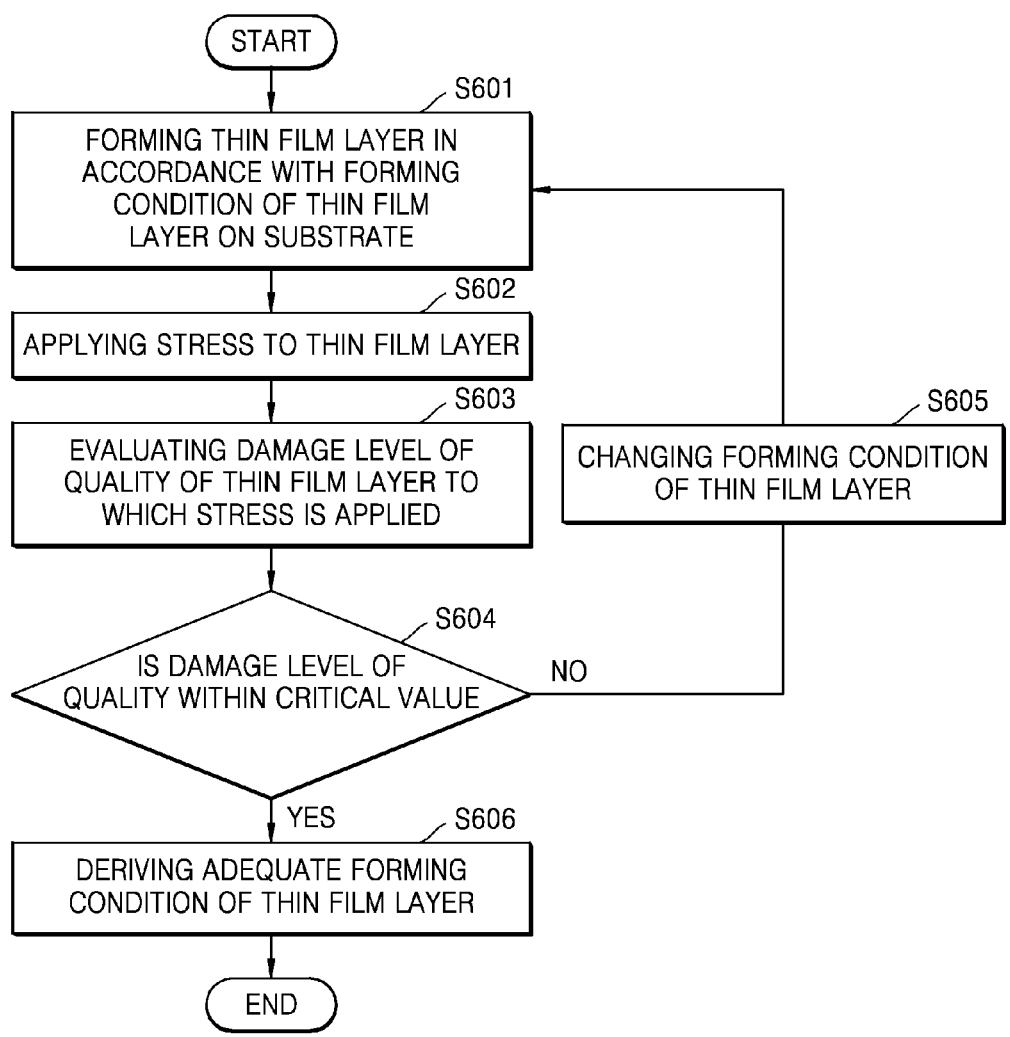
FIG. 30 is a flowchart of deriving an adequate fabrication condition for a thin film layer according to an exemplary embodiment.

FIG. 30 is a flowchart showing the derivation of an adequate fabrication condition for a thin film layer according to an exemplary embodiment. Referring to FIG. 30, the thin film layer may be formed on the substrate in accordance with a fabrication condition of the thin film layer (S601), stress may be applied to the formed thin film layer (S602), a level of quality deterioration in the thin film layer to which the stress is applied may be evaluated (S603), whether the level of the quality deterioration is within a critical value may be determined (S604), an adequate fabrication condition of the thin film layer may be derived when the level is within the critical value (S606), or the fabrication condition of the thin film layer may be changed when the level is outside the critical value (S605).

In the applying the stress to the thin film layer (S602), the stress may include the various kinds of stresses described above. For example, the stress may need to satisfy PCT conditions, and the stress may be applied over a time of less than about 100 hours. Since the steps from S601 to S604 need to be repeated in order to derive an adequate fabrication condition for the thin film layer (S606), the adequate fabrication condition of the thin film layer may be easily derived, since the time needed for applying the stress (S602) is shortened by the methods disclosed herein. Accordingly, the method of evaluating the quality of a thin film layer according to exemplary embodiments herein may significantly reduce the amount of evaluation time required, as compared with a conventional method, and thus an adequate fabrication condition of the thin film layer may be more easily derived.

In the evaluating the level of quality deterioration (S603), the level of quality deterioration may include evaluation of at least one of the refractive index change rate, the thickness change rate, the external quantum efficiency change rate, the dark current change rate, and the number of pinholes, which have been described above.

In the evaluating whether the level of quality deterioration is within a critical value (S604), the level of quality deterioration may be compared with the critical value described above. The critical value may be determined based on whether the quality of the thin film layer is "stable" or "unstable". For example, the critical value may be established using criterion including whether the thin film layer has a quality sufficient enough to protect a substrate or a device from outside moisture or oxygen. For example, when the refractive index change rate is compared with the critical value, a value of (n2−n1)/n1, which is the ratio of refractive index change rates of the thin film layer before and after stress application, may be compared with the critical value, as an example, the refractive index change rate may be compared with a critical value of about 5%. When the refractive index change rate is equal to or greater than the critical value of about 5%, the level of quality deterioration of the thin film layer may be determined as being beyond the critical value. As another example, the level of quality deterioration of the thin film layer may be determined by comparing the external quantum efficiency change rate with a critical value of about 5%. As another example, the level of quality deterioration of the thin film layer may be determined by comparing the dark current change rate with a critical value of about 5%. As another example, the level of quality deterioration of the thin film layer may be determined by comparing the number of pinholes with a critical value of 0.

In the changing the fabrication condition of the thin film layer (S605), when the quality of the thin film layer formed in accordance with a certain fabrication condition of the thin film layer (S601) is outside the critical value, the fabrication condition of the thin film layer may be changed to provide for forming a stable thin film layer.

In the deriving an adequate fabrication condition of the thin film layer (S606), when the quality of the thin film layer is within the critical value, the fabrication condition of the corresponding thin film layer may be deemed adequate.

Figure 31:
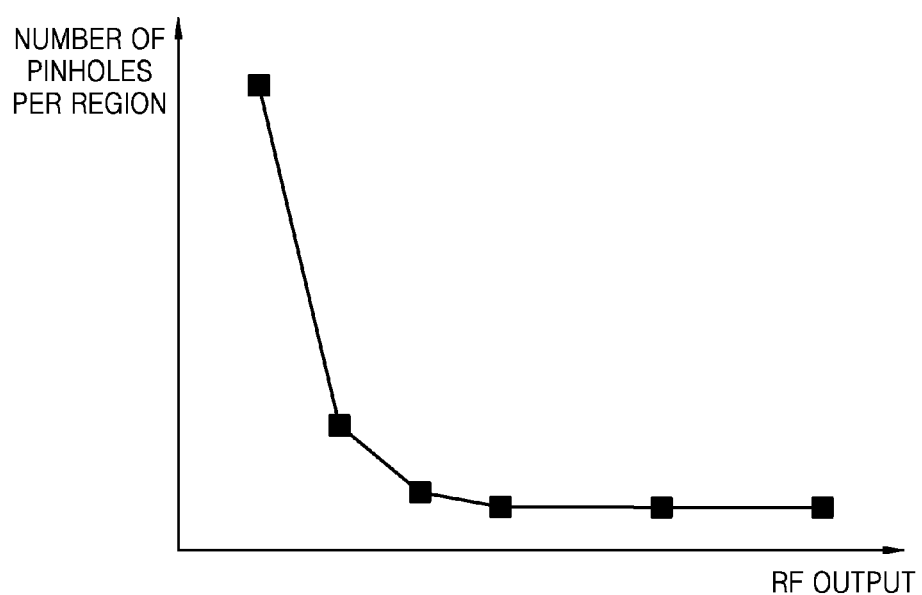
FIGS. 31 and 32 are graphs for identifying an adequate fabrication condition for a thin film layer according to FIG. 30.
Figure 32:
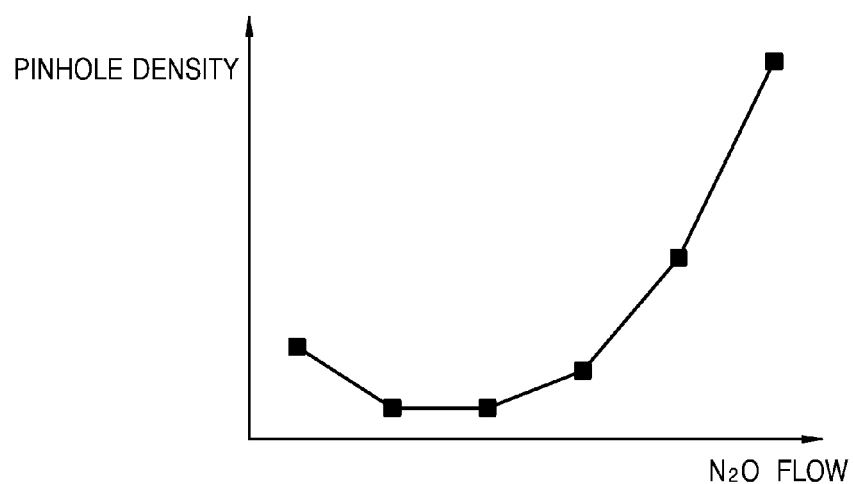

FIGS. 31 and 32 are graphs illustrating the identification of an adequate fabrication condition of the thin film layer according to FIG. 30.

Referring to FIG. 31, the horizontal axis denotes the radio frequency (RF) output W among fabrication conditions of the thin film layer and the vertical axis denotes the number of pinholes per region among quality deterioration. According to the illustrated graph, as the RF output increases, the number of pinholes per region may decrease. Accordingly, when the RF output is equal to or greater than a certain level, the fabrication condition for the thin film layer may be evaluated as being adequate.

Referring to FIG. 32, the horizontal axis denotes a $N_2O$ flow among the fabrication conditions of the thin film layer and the vertical axis denotes a pinhole density (the number/$cm^2$) among the quality deterioration. As illustrated in FIG. 32, the pinhole density may have a minimum value at a second or third point of the $N_2O$ flow. Accordingly, an adequate value for the $N_2O$ flow to reduce the quality deterioration of the thin film layer may be derived, and thus the fabrication condition of the thin film layer may be changed.

Figure 33:
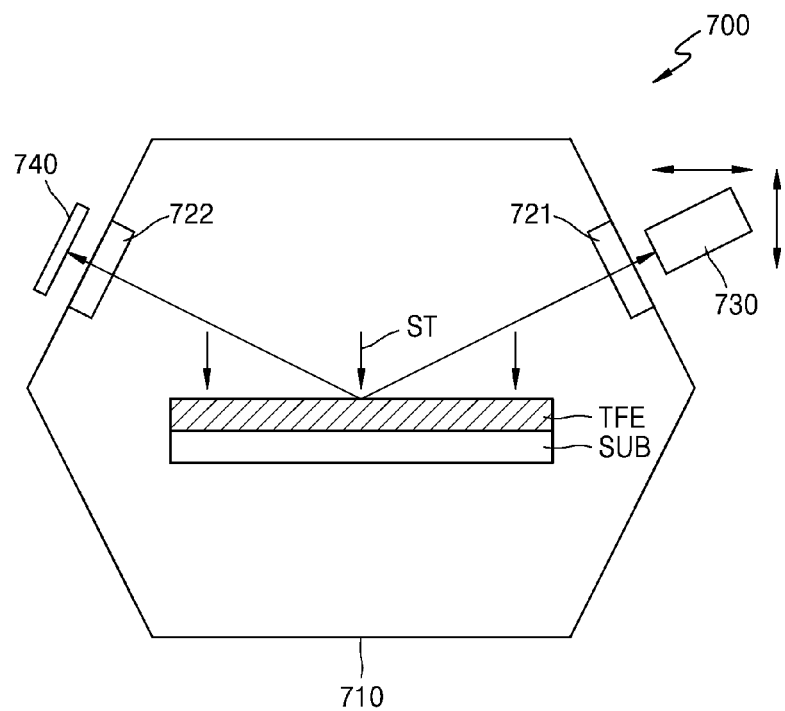
FIG. 33 illustrates an apparatus for evaluating the quality of a thin film layer according to an exemplary embodiment.

FIG. 33 illustrates an apparatus 700 for evaluating the quality of a thin film layer according to an exemplary embodiment. Referring to FIG. 33, the apparatus 700 for evaluating the quality of a thin film layer may include a stress chamber 710, a light source 730, and a sensor 740.

The stress chamber 710 may apply the stress ST to the thin film layer TFE. For example, the stress chamber 710 may apply the stress ST to the thin film layer TFE in accordance with a predetermined fabrication condition of the thin film layer TFE. For example, the stress chamber 710 may apply to the thin film layer TFE at least one of pressure stress, temperature stress, humidity stress, optical stress, tension stress, compression stress, and oxygen stress. As an example, the stress chamber 710 may apply the stress ST to the thin film layer TFE so that PCT conditions are satisfied.

The stress chamber 710 may include an internal space in which the substrate SUB and the thin film layer TFE thereon are prepared. In addition, the stress chamber 710 may include a first opening and a second opening through which light may pass. The stress chamber 710 may allow light to pass through the first opening, while the stress chamber 710 includes a first glass 721 sealing the inside thereof. The stress chamber 710 may allow light to pass through the second opening, while the stress chamber 710 includes a second glass 722 sealing the inside thereof.

The light source 730 may emit light that penetrates the first glass 721 and hits the thin film layer TFE. The sensor 740 may sense light that has been reflected from the thin film layer TFE and penetrated the second glass 722. The light source 730 and the sensor 740 may measure the refractive index change rate of the thin film layer TFE.

According to the present disclosure, the apparatus 700 for evaluating the quality of a thin film layer may apply the stress ST to the thin film layer TFE, cause the quality deterioration of the thin film layer TFE, and determine the level of the quality deterioration with respect to time by measuring the refractive index change rate.

In the method of evaluating the quality of a thin film layer according to exemplary embodiments described above, the number of substrates or a wafer substrates, which is an evaluation target, may be at least one. For example, thin film layers may be prepared on at least two wafer substrates and the qualities of the thin film layers on the at least two wafer substrates may be simultaneously evaluated.

In the method of evaluating the quality of a thin film layer according to exemplary embodiments described above, a plurality of chips may be prepared on a wafer substrate or a silicon substrate and the thin film layer may be prepared on the plurality of chips. For example, a chip yield or a device yield may be derived by measuring how many percent of chips on the wafer substrate are produced without defects. For example, when an entire wafer area is defined as $S_T$, an area occupied by the chips is defined as $S_C$, a dummy region area is defined as $S_D$, an edge exclusion area is defined as $S_E$, and the number of pinholes is defined as $N_P$, the chip yield η may be derived by the Formula 1.

$$\eta = 100\% - N_P * S_C / (S_T - S_D - S_E) \quad \text{[Formula 1]}$$

According to the present disclosure, the method of evaluating the quality of a thin film layer may reduce the evaluation time to dozens of hours from the conventional hundreds of hours needed by a water vapor transmission rate (WVTR) method or an oxygen transmission rate (OTR) method.

According to an exemplary embodiment herein, the method of evaluating the quality of a thin film layer may derive an adequate fabrication condition of the thin film layer.

According to the present disclosure, the method of evaluating the quality of a thin film layer may use conventional semiconductor processes and display processes, and thus, may provide easy evaluation and reduce cost.

According to an exemplary embodiment, the method of evaluating the quality of a thin film layer may measure a refractive index change or a thickness change and evaluate the quality of the thin film layer.

According to an exemplary embodiment, the method of evaluating the quality of a thin film layer may include forming the thin film layer on a device and evaluating the quality of the thin film layer, and thus, may provide for an evaluation of the quality of the thin film layer under the same conditions as real usage conditions.

According to an exemplary embodiment, the method of evaluating the quality of a thin film layer may simultaneously evaluate the qualities of a plurality of thin film layer samples.

According to an exemplary embodiment, the method of evaluating the quality of a thin film layer may include evaluating the quality of the thin film layer by measuring a change rate of electrical characteristics of the OPD device.

According to an exemplary embodiment, the method of evaluating the quality of a thin film layer may easily measure the number of pinholes in the thin film layer.

Descriptions of features or aspects within each embodiment should typically be considered as available for other similar features or aspects in other embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of evaluating a quality of a thin film layer, the method comprising the following steps in order:
    forming the thin film layer on a substrate;
    measuring a first refractive index of the thin film layer;
    applying a pressure cooker test (PCT) condition to the thin film layer;
    measuring a second refractive index of the thin film layer; and
    measuring the quality of the thin film layer by determining a refractive index change rate from the first refractive index and the second refractive index and comparing the determined refractive index change rate to a predetermined threshold change rate.

2. The method of claim 1, wherein the PCT condition includes a pressure stress, a temperature stress, and a humidity stress.

3. The method of claim 1, wherein the forming of the thin film layer comprises forming the thin film layer on the substrate via a thin film encapsulation process.

4. The method of claim 1, wherein the measuring the quality comprises comparing the first refractive index to the second refractive index.

5. The method of claim 1, wherein the pressure cooker test (PCT) condition comprises a temperature of 119-123° C., a humidity of 98 to 100%, and a pressure of 1.8-2.2 atm.

6. The method of claim 1, wherein the substrate is a wafer substrate comprising a plurality of chips and the thin film layer is formed on the plurality of chips.

7. The method of claim 1, wherein the forming of the thin film layer comprises forming the thin film layer using a radio frequency output, and
    wherein the method further comprises adjusting the radio frequency output based on the measured quality of the thin film layer.

8. The method of claim 1, wherein the forming of the thin film layer comprises forming the thin film layer using a $N_2O$ flow, and
    wherein the method further comprises adjusting the $N_2O$ flow based on the measured quality of the thin film layer.

9. A method of evaluating a quality of a thin film layer, the method comprising the following steps in order:
    forming the thin film layer on a substrate;
    measuring a first refractive index of the thin film layer;
    applying a pressure cooker test (PCT) condition to the thin film layer;
    measuring a second refractive index of the thin film layer; and
    measuring the quality of the thin film layer,
    wherein the measuring the quality comprises comparing the first refractive index to the second refractive index, and
    wherein the measuring the quality comprises not changing a forming condition of the thin film layer if the difference between the first refractive index and the second refractive index is less than 5% and changing the forming condition of the thin film layer if the difference between the first refractive index and the second refractive index is greater than or equal to 5%.

10. A method of evaluating a quality of a thin film layer, the method comprising the following steps in order:
    forming the thin film layer on a substrate;
    measuring a first refractive index of the thin film layer;
    applying a pressure cooker test (PCT) condition to the thin film layer;
    measuring a second refractive index of the thin film layer; and
    measuring the quality of the thin film layer,
    wherein the forming of the thin film layer comprises forming the thin film layer using a fabrication condition of the thin film layer, and
    the evaluating of the quality comprises evaluating a degree of quality deterioration in the thin film layer and comparing the degree of quality deterioration with a predetermined critical value.

11. The method of claim 10, wherein the evaluating of the quality comprises determining that the fabrication condition of the thin film layer is adequate when the degree of quality deterioration is within the predetermined critical value, and changing the fabrication condition of the thin film layer when the degree of quality deterioration is equal to or greater than the predetermined critical value.

* * * * *